US009028455B2

(12) United States Patent
Villette et al.

(10) Patent No.: US 9,028,455 B2
(45) Date of Patent: May 12, 2015

(54) CYLINDRICAL HOLDER FOR PHARMACEUTICAL PRODUCT CONTAINER INTENDED TO BE SET IN ROTATION

(75) Inventors: Olivier Villette, Andreze (FR); Denis Ripaud, Tilleries (FR)

(73) Assignee: Dentalhitec, Mazieres en Mauges (FR)

( * ) Notice: Subject to any disclaimer, the term of this patent is extended or adjusted under 35 U.S.C. 154(b) by 251 days.

(21) Appl. No.: 12/961,567

(22) Filed: Dec. 7, 2010

(65) Prior Publication Data

US 2011/0152780 A1 Jun. 23, 2011

(30) Foreign Application Priority Data

Dec. 17, 2009 (FR) ...................................... 09 59141

(51) Int. Cl.
| A61M 5/24 | (2006.01) |
| A61C 1/00 | (2006.01) |
| B65D 1/02 | (2006.01) |
| A61M 5/20 | (2006.01) |
| A61M 5/31 | (2006.01) |
| A61M 5/32 | (2006.01) |

(52) U.S. Cl.
CPC .. A61M 5/24 (2013.01); A61C 1/00 (2013.01); A61M 5/20 (2013.01); A61M 5/3129 (2013.01); A61M 2005/2407 (2013.01); A61M 2005/2437 (2013.01); A61M 2005/3289 (2013.01); A61M 2202/0241 (2013.01); A61M 2210/0625 (2013.01); A61M 2210/0637 (2013.01); B65D 1/0223 (2013.01)

(58) Field of Classification Search
CPC .......... A61M 5/24; A61M 2005/2407; A61M 2005/2433; A61M 2005/243; A61M 2005/3289

USPC .............. 604/93.01, 131, 181, 187, 197, 218, 604/227, 232, 234, 235
See application file for complete search history.

(56) References Cited

U.S. PATENT DOCUMENTS

| 1,718,591 | A | * | 6/1929 | Smith ........................... 604/234 |
| 5,590,782 | A | | 1/1997 | Haber et al. |
| 5,927,976 | A | | 7/1999 | Wu |
| 6,245,043 | B1 | | 6/2001 | Villette |
| 2005/0283115 | A1 | * | 12/2005 | Giambattista et al. ........ 604/110 |
| 2006/0106363 | A1 | | 5/2006 | Aravena et al. |
| 2009/0030376 | A1 | * | 1/2009 | Teufelberger et al. ........ 604/188 |
| 2009/0093769 | A1 | * | 4/2009 | Wright et al. .................. 604/178 |
| 2009/0107947 | A1 | | 4/2009 | Knaack |

FOREIGN PATENT DOCUMENTS

| EP | 2 022 522 A1 | 2/2009 |
| FR | 822 764 A | 1/1938 |

(Continued)

*Primary Examiner* — Kami A Bosworth
(74) *Attorney, Agent, or Firm* — Leydig, Voit & Mayer, Ltd.

(57) ABSTRACT

A cylindrical holder for housing a pharmaceutical product container in a hand-piece of a surgical instrument for perforating dense tissue of a human or animal body and injecting a pharmaceutical product behind or in the tissue. The cylindrical holder connects an injection needle with the container. The holder has a tubular wall for receiving the container. The tubular wall includes contact areas defined by bridges of material subsisting between cut-outs located along circumferential rows, the bridges of material having deflections towards the inside of the cylindrical holder. A surgical instrument for perforating dense tissue of a human or animal body and injecting a pharmaceutical product behind or in the tissue, and includes a hand-piece and the cylindrical holder.

9 Claims, 2 Drawing Sheets

(56) References Cited

FOREIGN PATENT DOCUMENTS

Figure 1:
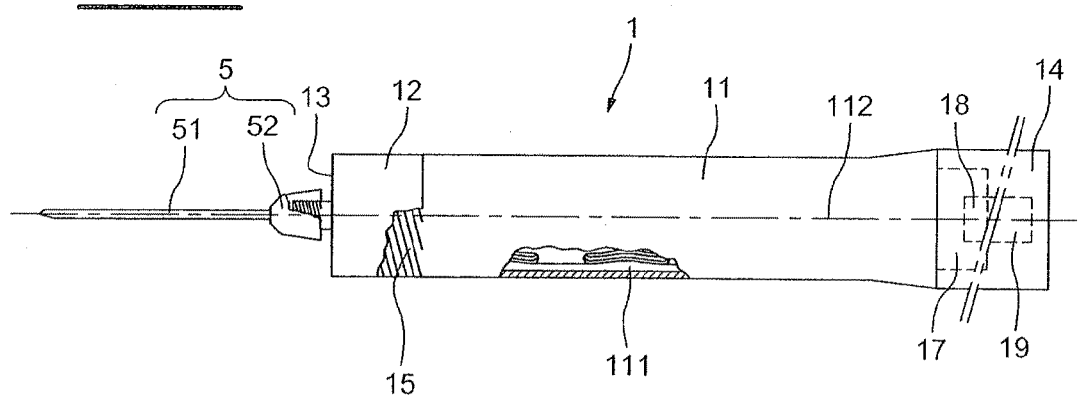

| FR | 1 238 213 A | 8/1960 |
| FR | 2 540 385 A1 | 8/1984 |
| WO | WO 2006/007590 A2 | 1/2006 |
| WO | WO 2007/018809 A2 | 2/2007 |

* cited by examiner

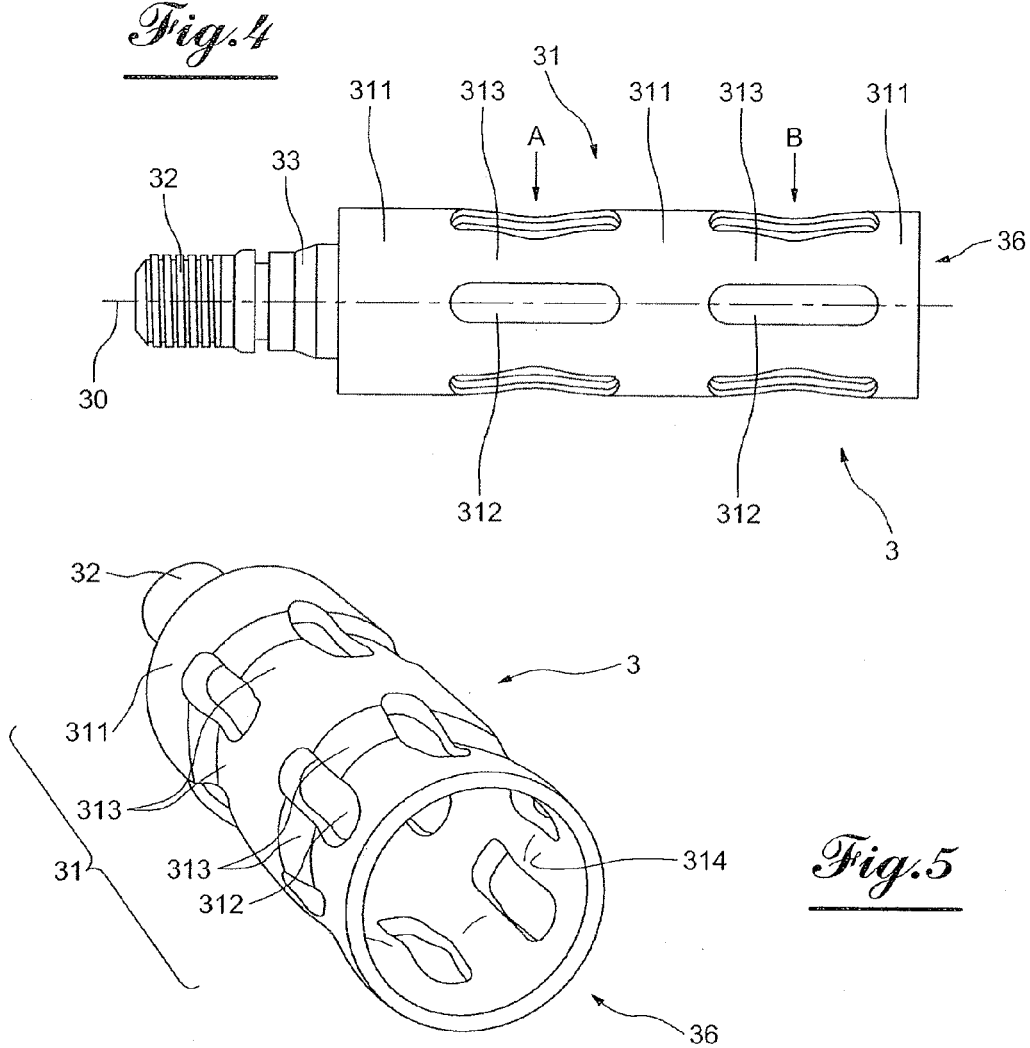
*Fig.4*
*Fig.5*
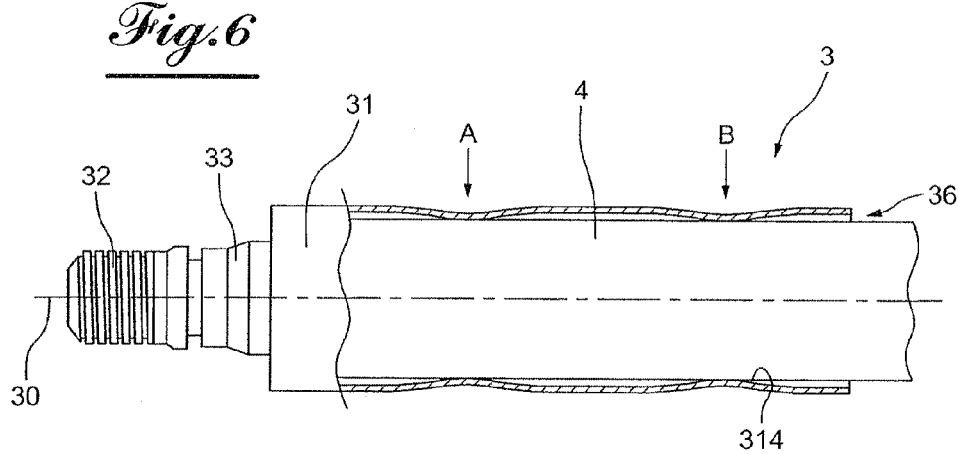
*Fig.6*

CYLINDRICAL HOLDER FOR PHARMACEUTICAL PRODUCT CONTAINER INTENDED TO BE SET IN ROTATION

BACKGROUND

The present invention concerns a cylindrical holder for a container containing a pharmaceutical product. More particularly, the invention concerns a cylindrical holder to be joined in rotation with the container when this container is fitted into the holder. The holder/container assembly is then inserted in a hand-piece of a surgical instrument to perforate dense tissue in a human or animal body and to inject a pharmaceutical product into the same body.

BACKGROUND

In some medical applications, for example in the field of dental anaesthesia, it is necessary to pass through dense tissue, e.g., the cortical bone of a jawbone to inject a pharmaceutical product at the proper site. To arrive thereat, first a drill is used for perforation followed by injection using a needle. According to an alternative method, a perforator needle is used to perforate and also to inject.

If a needle is used for perforation, the simplest means, which requires least space, is to use the container of the anaesthetic product as transmission shaft between the driving means and the needle. An adaptor part must therefore be designed capable of transmitting the torque of the pharmaceutical product container to the perforator needle. The adapter part must be perfectly coaxial with the container to withstand the high rotation speeds without generating vibrations or too much noise. In addition, the adapter part must be capable of being sterilized at high temperatures (between 130 and 140° C.) since the perforator needle, and frequently also the end of the adapter part receiving the needle, are in contact with the patient, and notably in the patient's mouth.

The adapter parts used prior to the invention are formed in plastic materials which use the deformation of the material to grip the container and thereby transmit torque to the perforator needle. However, the materials used have proved to be disadvantageous insofar as they show early wearing due to high internal stresses when adapting to the different diameters of the containers. These high internal stresses prevent fitting over long distances, which is adverse to the coaxiality of rotation of the container relative to the needle.

Other plastic holders have a length close to the length of the containers and, to adapt to the different container diameters, they have rubber rings hence inner ring seals housed in annular grooves provided for this purpose in the holders.

However, these holders have proved to have shortcomings on account of the poor resistance of the rubber products over time to sterilisation when they are confronted with temperatures of between 130° C. and 140° C. and to cleaning products. Additionally, the rubber seals cause an increase in the outer diameter of the holder. This increase leads to an increase in the diameter of the hand-piece which gives rise to a major problem insofar as it is always sought to obtain maximum ease of handling, optimal vision and small volume.

Regarding glass containers, through their manufacturing mode these show major variations in diameter and length. Some models are also provided with an anti-breakage plastic film which further increases variations in diameter and modifies the contact surface imparting poor sliding properties for the rubber seals.

SUMMARY OF THE INVENTION

The object of the invention is therefore to propose means which can remedy the above-described disadvantages.

The object of the invention is achieved with a cylindrical holder to house a pharmaceutical product container in the hand-piece of a surgical instrument designed for perforating dense tissue in a human or animal body and for injecting a pharmaceutical product behind or in this dense tissue, the cylindrical holder being adapted to connect an injection needle to the container and comprising a tubular wall adapted to receive the container.

According to the present invention, the tubular wall comprises contact areas formed by bridges of material subsisting between cut-outs provided along circumferential rows, the bridges of material having deflections towards the inside of the cylindrical holder.

The cylindrical holder of the invention may also have at least one of the following additional characteristics, taken alone or in any technically possible combination:
- the cut-outs are arranged in at least one circumferential row;
- the bridges of material are adapted to cause the cylindrical holder to be joined in rotation with the container it receives;
- the bridges of material have bend lines transverse to a longitudinal axis of the cylindrical holder and projecting into the holder;
- the holder comprises two circumferential rows of cut-outs spaced apart along a longitudinal axis of the cylindrical holder;
- the cut-outs are oblong holes oriented parallel to the longitudinal axis of the cylindrical holder;
- the holder is made in a rigid plastic material.

The cylindrical holder of the invention can be made in plastic materials which fully withstand sterilization and cleaning products. The fact that these materials are often very rigid is offset by the fact that the cylindrical holder has a specific inner shape which sets up a contact area with the container at the ends, or close to each of the ends, of the cylindrical holder to provide optimal coaxiality. The contact areas are formed by bridges of material subsisting between the cut-outs made along the lines of circumferential rows, the bridges of material having deflections towards the inside of the cylindrical holder.

By means of this arrangement of the invention, a certain amount of elasticity is imparted to the tubular body of the cylindrical holder, enabling it permanently to adapt to variations in diameter of the anaesthesia containers used and to distribute strain in equal manner over the bridges of material. At the same time, the cylindrical holder is able to transmit sufficient torque within a minimum volume, and well withstands the stresses of cleaning and sterilisation. When the container is inserted in the cylindrical holder, the deflection of the bridges of material is elastically reduced, and when the container is withdrawn they resume their initial shape.

The purpose of the invention is also achieved with a surgical instrument intended to perforate dense tissue of a human or animal body and to inject a pharmaceutical product behind or in the same tissue, the instrument comprising a hand-piece adapted to receive a cylindrical holder allowing a pharmaceutical product container to be housed in the hand-piece that can freely rotate about a longitudinal axis of the container, and to connect a perforator needle to the container, the hand-piece being provided with an axial throughway for the needle.

According to the present invention, the cylindrical holder comprises a tubular wall provided with contact areas formed by bridges of material subsisting between cut-outs provided along circumferential rows, the bridges of material having deflections towards the inside of the cylindrical holder.

BRIEF DESCRIPTION OF DRAWING FIGURES

Figure 2:
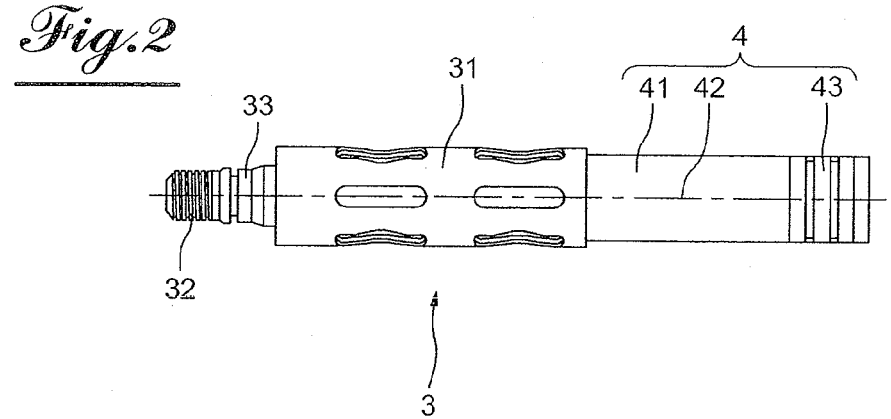
Figure 3:
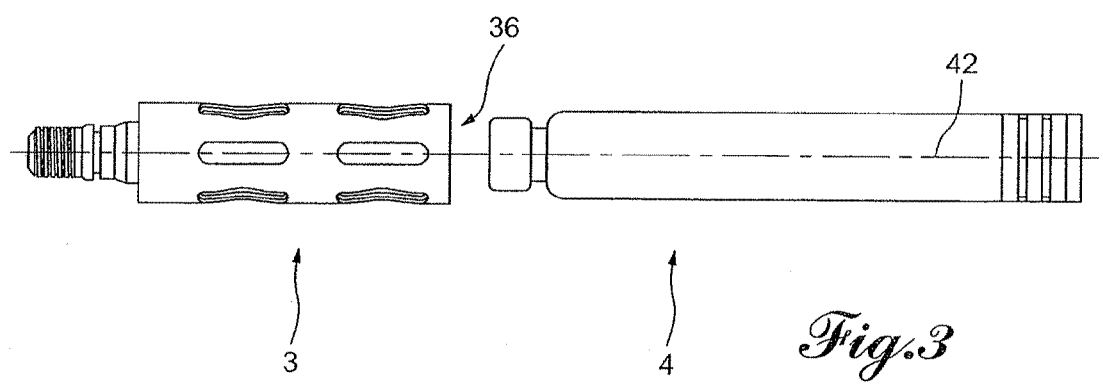

Other characteristics and advantages of the present invention will become apparent from the following description of one embodiment of the invention. The description is given with reference to the drawings in which:

FIG. 1 illustrates a surgical instrument according to the invention,

FIG. 2 shows a cylindrical holder with a cartridge as container of a pharmaceutical product, in the assembled state, FIG. 3 shows the cylindrical holder and the separated cartridge, FIG. 4 shows a cylindrical holder from a side view, FIG. 5 shows a cylindrical holder from a perspective side view of the axial opening, and FIG. 6 shows the holder in FIGS. 4 and 5 along an axial section, with a container engaged in the cylindrical holder.

DETAILED DESCRIPTION

FIG. 1 is a schematic side view, with cutaway, of a surgical instrument according to the invention.

The instrument comprises a hand-piece 1 having an elongate body 11 with a housing 111 and two opposite ends 12, 14. The end 12 is formed by a removable head provided with an axial throughway 13. The head 12 is advantageously conformed to be attached to the body 11 by screwing, the body 11 being provided for this purpose with a thread 15 and the head 12 with a mating thread. However, the head 12 could just as well be fixed by press-fitting or it could be integrated in the body 11 so as only to form a single part. The end 14 of the hand-piece 1 is formed by a bottom part mounted by press-fitting or, according to an embodiment that is not illustrated, by screwing onto a connector 17 of the body 11.

The body 11 of the hand-piece 1 is conformed so that in the housing 111 which is symmetrical in rotation about an axis 112, it can receive a cylindrical holder 3 and a container 4 for a pharmaceutical product, the pharmaceutical product being a solution for injection. The container 4, also called a cartridge, comprises a rotating cylindrical body 41 with an axis 42 and a piston 43 to act on the content. When in use the container 4 is fitted into the cylindrical holder 3 as shown FIG. 2.

The cylindrical holder 3 is a hollow elongate element with a neck provided with a threaded part 32 at one of its two opposite ends and with an axial opening 36 to insert the container 4 at the other end. The holder 3 is formed so that the neck is housed within the axial throughway 13 of the head 12 of the hand-piece 1 and projects outwardly from the latter via the threaded part 32 of the neck so that it is able to receive a perforator needle 5 by screwing. For this purpose the needle 5, in addition to a cannula 51, comprises a threaded end piece 52 for attachment.

The bottom part 14 maintains the cylindrical holder 3 inside the elongate body 11 and holds it bearing against an inner part of the head 12 conformed for this purpose. In addition, the bottom part 14 comprises a member 18 conformed to bear against a piston 43 of the container 4 to exert pressure on the pharmaceutical product contained in the container 4. The member 18 is configured not only to allow the injection of a determined dose of the pharmaceutical product into the human or animal body, but also to insert the pharmaceutical product once or several times into the needle 5 and to hold it under pressure in accordance with operating criteria described below in the remainder of the description. The bottom part 14 also houses driving means 19 used to set the holder/container assembly in rotation about the longitudinal axis 42 of the body 41 of the container 4.

FIGS. 2 and 3 respectively illustrate an assembled state and a separated state of the cylindrical holder 3 and the pharmaceutical product container 4. The cylindrical holder 3 comprises a hollow or tubular elongate body 31 having a longitudinal axis 30. The body 31 is made in a rigid plastic material and is closed at one of its two opposite ends by the above-mentioned neck. At the other end, the body 31 is provided with an axial opening 36 in which to fit a container 4. The neck comprises a threaded part 32 to carry the perforator needle 5 and is provided with a lumen through which the needle 5 first enters inside the body 31 and then passes through the elastic membrane of the container 4 to arrive inside this container. Therefore, by pressing on the piston 43, the pharmaceutical product leaves the container 4 via the needle 5 and is injected into a human or animal body. The neck is also provided with a circumferential bearing raceway 33 intended to and conformed to cooperate with a mechanical bearing (not illustrated) arranged in the head 12 of the hand-piece 1 and intended to reduce rotational resistance when the surgical instrument is used in perforation mode.

FIGS. 4 and 5 show the cylindrical holder 3 alone from a side view and a perspective view respectively. The body 31 of the cylindrical holder 3 is essentially a tubular element of constant outer diameter over the entire axial length of the body 31 as evidenced by the solid wall parts 311. The exception to the characteristic of constant outer and inner diameters lies in two parts of the body 31 where cut-outs and bridges of material are arranged alternately in two circumferential rows A, B.

To impart certain elasticity to the body 31, which is needed to grip the container 4, the body 31 is provided with cut-outs 312 formed at circumferential distances that are at least approximately equal around the entire periphery of the body 31 and in at least one circumferential row, preferably in two circumferential rows A, B. The cut-outs 312 here are in the form of oblong holes extending along axes parallel to the longitudinal axis 30 of the cylindrical holder 3.

Between the cut-outs 312 of one same row bridges of material 313 subsist deflected inwardly inside the tubular body 31, so that they can cooperate elastically with a container 4 thus gripped inside the body 31. The bridges of material 313 are arranged so as to take hold of the container 4 when it is inserted inside the holder 3, close to the ends of the holder 3 to obtain the greatest axial stability of the container 4 relative to the perforator needle 5.

As shown FIG. 6 giving a perspective view of the opening 36 of the cylindrical holder 3, the inward deflection of the bridges of material 313 creates inner sloped parts 314. When a container 4 is inserted in the cylindrical holder, the container 4 comes to bear on the slopes 314 of the bridges of material 313 and separates them radially from each other countering the force exerted by the bridges of material 313. This arrangement ensures permanent coaxial seating of the container 4 relative to the cylindrical holder 3. At the same time when the container 4 is removed from the cylindrical holder 3, the bridges of material 313 deflect inwardly i.e. they resume their initial deflection shape.

This arrangement of the invention renders the use of rubber seals or other additional elastic means superfluous and, with the sole elasticity of the bridges of material 313, it ensures the adaptation of the holder 3 to the different outer diameters of containers 4.

The invention claimed is:

1. A surgical instrument for perforating a human or animal body and injecting a pharmaceutical product into the human or animal body, the surgical instrument comprising:
   an elongate hand-piece having opposed first and second ends, a head at the first end that includes a central throughway, and an outer wall circumferentially disposed with respect to a central axis of the elongate hand-piece, wherein the outer wall encloses an interior volume that extends from the first end to the second end of the outer wall;
   a tubular holder disposed partially within the interior volume of the elongate hand-piece, and rotatable with respect to the elongate hand-piece, about the central axis of the hand-piece, wherein the tubular holder has a central axis and includes
      a first tubular portion having opposed first and second ends and a wall,
      a second tubular portion comprising a neck at and protruding from and beyond the first end of the first tubular portion of the tubular holder, wherein the neck extends through the central throughway in the head of the elongate hand-piece and outside the interior volume of the hand-piece, at the first end of the elongate hand-piece, and includes a passage for a needle, and,
      at a first location of the first tubular portion of the tubular holder, along the central axis of the tubular holder, first and second cut-outs extending entirely through the wall of the first tubular portion and arranged circumferentially in the wall of the first tubular portion with respect to the central axis of the tubular holder, wherein
         parts of the wall of the first tubular portion separating the first and second cut-outs from each other constitute first and second bridge portions of the wall of the first tubular portion, which are continuous parts of the first tubular portion, and
         the first and second bridge portions of the wall of the first tubular portion resiliently deflect toward the central axis of the tubular holder so that the first tubular portion has a smaller internal diameter at the first and second bridge portions than at the first and second ends of the first tubular portion;
   a pharmaceutical product container disposed partially within the tubular holder and entirely within the interior volume of the elongate hand-piece, wherein
      the pharmaceutical product container has an outer cylindrical surface,
      the first and second bridge portions contact and transmit torque to the outer cylindrical surface of the pharmaceutical product container from the tubular holder so that the pharmaceutical product container rotates with respect to the elongate hand-piece when the tubular holder is rotated relative to the elongate hand-piece; and
   a perforating needle passing through the neck of the tubular holder, fixedly held in the neck of the tubular holder, and connected to the pharmaceutical product container for delivering a pharmaceutical product from within the pharmaceutical product container while the tubular holder and the pharmaceutical product container are rotated about the central axis of the tubular holder, relative to the elongate hand-piece.

2. The surgical instrument according to claim 1, wherein the neck of the tubular holder includes external threads and further including a threaded end-piece engaging the external threads and fixing the perforating needle to the tubular holder.

3. The surgical instrument according to claim 1 further including a connector mounted on and closing the second end of the elongate hand-piece.

4. The surgical instrument according to claim 1, wherein the first end of the elongate hand-piece is threaded and the head includes a threaded head-piece detachably mounted on the first end of the elongate hand-piece and including the central throughway through which the neck of the tubular holder passes.

5. The surgical instrument according to claim 1, wherein the first and second cut-outs are first and second oblong holes in the wall of the first tubular portion and the first and second oblong holes are oriented parallel to the central axis of the tubular holder.

6. The surgical instrument according to claim 5, wherein
   the first and second bridge portions of the wall of the first tubular portion are parts of the first tubular portion, and
   central portions of the first and second bridge portions of the wall of the first tubular portion resiliently deflect toward the central axis of the tubular holder so that the first tubular portion has a smaller internal diameter at the central portions of the first and second bridge portions than at first and second longitudinal ends of the first and second oblong holes of the first tubular portion.

7. The surgical instrument according to claim 1, including, at a second location of the first tubular portion of the tubular holder, along the central axis of the tubular holder, spaced from the first location, third and fourth cut-outs extending entirely through the wall of the first tubular portion and arranged circumferentially in the wall of the first tubular portion with respect to the central axis of the tubular holder, wherein
   continuous parts of the wall of the first tubular portion separating the third and fourth cut-outs from each other constitute third and fourth bridge portions of the wall of the first tubular portion,
   the third and fourth bridge portions of the wall of the first tubular portion resiliently deflect toward the central axis of the tubular holder so that the tubular holder has a smaller internal diameter at the third and fourth bridge portions than at the first and second ends of the first tubular portion, and
   the third and fourth bridge portions contact and transmit torque to the outer cylindrical surface of the pharmaceutical product container from the tubular holder when the tubular holder is rotated about the central axis of the tubular holder, relative to the elongate hand-piece.

8. The surgical instrument according to claim 7, wherein the third and fourth cut-outs are third and fourth oblong holes in the wall of the first tubular portion and the third and fourth oblong holes are oriented parallel to the central axis of the tubular holder.

9. The surgical instrument according to claim 8, wherein
   the third and fourth bridge portions of the wall of the first tubular portion are parts of the first tubular portion, and
   central portions of the third and fourth bridge portions of the wall of the first tubular portion resiliently deflect toward the central axis of the tubular holder so that the first tubular portion has a smaller internal diameter at the central portions of the third and fourth bridge portions than at first and second longitudinal ends of the third and fourth oblong holes of the first tubular portion.

* * * * *